United States Patent [19]

Ruppel et al.

[11] Patent Number: 5,739,391
[45] Date of Patent: Apr. 14, 1998

[54] CATALYTIC GAS-PHASE OXIDATION OF ACROLEIN TO ACRYLIC ACID

[75] Inventors: Wilhelm Ruppel, Frankenthal; Ulrike Wegerle, Worms; Andreas Tenten, Neustadt; Ulrich Hammon, Mannheim, all of Germany

[73] Assignee: BASF Aktiengesellschaft, Ludwigshafen, Germany

[21] Appl. No.: 525,118

[22] Filed: Sep. 8, 1995

[30] Foreign Application Priority Data

Sep. 8, 1994 [DE] Germany ................ 44 31 949.5

[51] Int. Cl.$^6$ ................................................. C07C 51/16
[52] U.S. Cl. ................................... 562/532; 562/535
[58] Field of Search ................................. 562/532, 535

[56] References Cited

U.S. PATENT DOCUMENTS

| | | |
|---|---|---|
| 3,566,961 | 3/1971 | Lorenz et al. . |
| 3,775,474 | 11/1973 | Ohara et al. . |
| 3,865,555 | 2/1975 | Elebracht et al. . |
| 3,871,445 | 3/1975 | Wanka et al. . |
| 3,893,951 | 7/1975 | Grasselli et al. . |
| 3,901,659 | 8/1975 | Joklik et al. . |
| 3,954,855 | 5/1976 | Wada et al. . |
| 4,075,127 | 2/1978 | Kadowaki et al. . |
| 4,203,906 | 5/1980 | Takada et al. . |
| 4,256,783 | 3/1981 | Takada et al. . |
| 4,259,211 | 3/1981 | Krabetz et al. . |
| 4,297,247 | 10/1981 | Krabetz et al. . |
| 4,339,355 | 7/1982 | Decker et al. . |
| 4,365,087 | 12/1982 | Kadowaki et al. . |
| 4,873,368 | 10/1989 | Kadowaki et al. . |
| 4,885,734 | 12/1989 | Yuzo . |
| 5,144,091 | 9/1992 | Martan et al. . |
| 5,177,260 | 1/1993 | Kawajiri et al. . |
| 5,198,578 | 3/1993 | Etzkorn et al. . |
| 5,264,625 | 11/1993 | Hammon et al. . |

FOREIGN PATENT DOCUMENTS

| | | |
|---|---|---|
| 2114681 | 8/1994 | Canada . |
| 0 427 508 | 5/1991 | European Pat. Off. . |
| 0 253 409 | 11/1991 | European Pat. Off. . |
| 0 468 290 | 1/1992 | European Pat. Off. . |
| 1 039 040 | 3/1959 | Germany . |
| 16 01 162 | 10/1970 | Germany . |
| 16 75 501 | 6/1972 | Germany . |
| 2 201 528 | 11/1972 | Germany . |
| 2 310 517 | 9/1973 | Germany . |
| 2 231 557 | 1/1974 | Germany . |
| 26 35 031 | 7/1977 | Germany . |
| 26 26 887 | 12/1977 | Germany . |
| 28 30 765 | 1/1980 | Germany . |
| 30 02 829 | 7/1980 | Germany . |
| 29 09 671 | 10/1980 | Germany . |
| 30 42 468 | 6/1981 | Germany . |
| 31 51 805 | 7/1983 | Germany . |
| 41 32 263 | 4/1993 | Germany . |
| 43 02 991 | 8/1994 | Germany . |
| 843663 | 8/1960 | United Kingdom . |
| 1252347 | 11/1971 | United Kingdom . |

OTHER PUBLICATIONS

Multitubular Reactor Design for Waste Minimization; R. Maciel Filho et al.; Institution of Chemical Engineers pp. 208–214, Transicheme, vol. 71, part B, Aug. 1993.

*Primary Examiner*—Samuel Barts
*Attorney, Agent, or Firm*—Oblon, Spivak, McClelland, Maier & Neustadt, P.C.

[57] ABSTRACT

A process for the catalytic gas-phase oxidation of acrolein to acrylic acid in a multiple contact tube fixed-bed reactor through whose space surrounding the contact tubes only one heat-exchange medium circuit is passed, at elevated temperature on catalytically active multimetal oxides with an acrolein conversion for a single pass of $\geq 95$ mol % and an acrylic acid formation selectivity of $\geq 90$ mol %, which comprises firstly passing the heat-exchange medium through the multiple contact tube fixed-bed reactor longitudinally, considered over the reaction container as a whole, to the contact tubes in cocurrent to the reaction-gas mixture and secondly superposing a transverse flow within the reaction container by means of an arrangement of successive baffles along the contact tubes which leaves passage cross sections free, so as to give a meandrous flow of the heat-exchange medium, seen in longitudinal section through the contact tube bundle, and setting the flow rate of the circulated heat-exchange medium so that its temperature rises by from 2° to 10° C. between the point of entry into the reactor and the point of exit out of the reactor.

17 Claims, No Drawings

CATALYTIC GAS-PHASE OXIDATION OF ACROLEIN TO ACRYLIC ACID

The present invention relates to a novel process for the catalytic gas-phase oxidation of acrolein to acrylic acid in a multiple contact tube fixed-bed reactor through whose space surrounding the contact tubes only one heat-exchange medium circuit is passed, at elevated temperature on catalytically active multimetal oxides with an acrolein conversion for a single pass of ≧95 mol % and an acrylic acid formation selectivity of ≧90 mol %.

The catalytic gas-phase oxidation of acrolein to acrylic acid is known in general terms and is particularly important as the second oxidation step in the preparation of acrylic acid by two-step catalytic gas-phase oxidation of propene in two successive reaction steps (cf., for example, DE-A 30 02 829). Acrylic acid is an important monomer which is used as such or in the form of its alkyl ester for the preparation of polymers which are suitable, for example, as adhesives.

The gas-phase oxidation of acrolein to acrylic acid is highly exothermic; for this reason, as a consequence of the wide range of possible parallel or subsequent reactions, it is necessary to control the variations in reaction temperature to a certain extent in order to give highly selective conversion of acrolein into acrylic acid and to enable the gas-phase oxidation to be carried out at all in a controllable manner.

A widely used method of controlling the heat of reaction being liberated comprises diluting the reactants oxygen and acrolein with inert gases, such as $N_2$, carbon oxides, such as $CO_2$ and CO, hydrocarbons, recycled reaction offgases and/or steam, it being particularly advantageous to use dilution gases having very high molar heat capacities (cf. EP-B 253 409).

Another generally used method of controlling the reaction temperature comprises carrying out the catalytic gas-phase oxidation of propene to acrolein in a multiple contact tube fixed-bed reactor. Such reactors correspond in design to shell-and-tube heat exchangers, ie. they usually comprise a generally cylindrical container in which a multiplicity of tubes (a tube bundle) corresponding to the cooling tubes of a shell-and-tube heat exchanger is accommodated, usually in a vertical arrangement. These contact tubes, each of which contains a fixed-bed arrangement of the appropriate catalytically active multimetal oxide, are installed with their ends in tubesheets in a sealing manner, and each runs into a bonnet, which is connected to the container at the upper or lower end. The reaction-gas mixture flowing through the contact tubes is fed in and removed via these bonnets, so that each contact tube corresponds to an extended reaction unit zone.

Furthermore, heat-exchange media are passed through the space surrounding the contact tubes in order to control the process heat. After leaving the container, the heat-exchange media, are restored to their original temperature, for example in external heat exchangers, before re-entering the reaction container (cf., for example, DE-A 30 242 468).

If heat-exchange medium enters the reactor at various (a plurality of) points along the contact tubes, we will refer here to the use of a plurality of heat-exchange medium circuits. If the heat-exchange medium enters only at one point, we will refer here to a single heat-exchange medium circuit, even if this circuit is not operated by means of one pump, but instead, for reasons of expediency, by means of a plurality of pumps.

The contact tubes are usually made of ferritic steel and typically have a wall thickness of from 1 to 3 mm. Their internal diameter is generally from 20 to 30 mm. The tube length normally extends to a few meters (a typical contact tube length is in the range from 2 to 4 m). For technical reasons, a number of contact tubes accommodated in the container is expediently at least 5000, preferably at least 10,000. The number of contact tubes accommodated in the reaction container is frequently from 15,000 to 30,000. Tube-bundle reactors with more than 40,000 contact tubes are something of an exception. Within the container, the contact tubes are normally homogeneously distributed, distribution expediently being selected so that the distance between the central internal axes of contact tubes lying closest to one another (the contact tube spacing) is from 35 to 45 mm (cf., for example, EP-468 290). Suitable heat-exchange media are, in particular, fluid temperature-controlled media. Particularly favorable is the use of melts of salts such as potassium nitrate, potassium nitrite, sodium nitrite and/or sodium nitrate, or of low-melting metals, such as sodium, mercury and alloys of various metals.

DE-A 26 35 031 discloses controlling the variations in reaction temperature in the catalytic gas-phase oxidation of acrolein to acrylic acid in a multiple contact tube fixed-bed reactor for acrolein conversions for a single pass of greater than 95 mol % by surrounding the contact tubes with a salt melt at 270° C.

DE-A 30 42 468 and DE-A 30 02 829 recommend passing the heat-exchange medium and reaction-gas mixture in cocurrent through the multiple contact tube fixed-bed reactor in order to smooth out the temperature distribution within the catalyst beds. In order that a high proportion of the contact tubes participate equally in the reaction proceedings, the prior art (for example German Patent 16 01 162) recommends aiming at a very homogeneous temperature of the heat-exchange medium in a horizontal section through the reactor (perpendicular to the reactor axis). The prior art furthermore recommends passing the heat-exchange medium through the reactor rapidly in order to dissipate the liberated heat of reaction as effectively as possible. It is recommended that the heat-exchange medium is circulated in such a way that the temperature difference between the heat-exchange medium employed between the point of entry and exit from the reactor is negligible.

A general problem in the catalytic gas-phase oxidation of acrolein to acrylic acid in multiple contact tube fixed-bed reactors is that the reaction temperature in the flow direction along a contact tube passes through a maximum, known as a hot spot. This shortens the life of the catalyst in this contact tube section and also impairs the selectivity of acrylic acid formation.

Various countermeasures against these disadvantages have already been recommended in the prior art. One proposal comprises reducing the diameter of the contact tubes and thus increasing the heat dissipation per unit volume of the catalyst. However, this method has the disadvantage that it inevitably increases the number of catalyst-filled contact tubes required for a certain production output, which increases both production costs of the reactor and the time necessary for filling and emptying the contact tubes with catalyst.

In another proposed process, it is attempted to suppress the formation of hot spots by varying the volume-specific activity of the catalytic charge along the contact tubes. However, this procedure inevitably requires either the use of at least two catalysts of different activity or the additional use of inert material. Furthermore, this procedure inevitably complicates filling of the contact tubes (an overview of the various countermeasures proposed is given, for example, in German Patent 28 30 765). Another obvious way of reducing the formation of hot spots comprises reducing the acrolein flow rate into the reactor. However, this measure also reduces the space-time yield of the target product.

DE-A 41 32 263 recommends carrying out the catalytic gas-phase oxidation of acrolein to acrylic acid in such a way that the reaction temperature in the flow direction along the contact tubes is from 260° to 300° C. as far as the point where an acrolein conversion of from 20 to 40 mol % is achieved, and the reaction temperature is subsequently lowered by a total of from 5° to 40° C., abruptly or successively, stepwise or continuously along the contact tubes as far as the point where an acrolein conversion of $\geq 95$ mol % is achieved, with the proviso that the reaction temperature in this second reaction zone is not below 240° C. However, this procedure has the disadvantage that the establishment of such a temperature profile requires the use of more than one heat-exchange medium circuit.

In addition to the possibility of simply conveying the heat-exchange medium essentially directly longitudinally to the contact tubes, DE-A 22 01 528 also comprises the possibility, for exothermic, catalytic, multiple contact tube fixed-bed oxidations, of accomplishing this longitudinal conveying merely considered over the reaction container as a whole and superposing a transverse flow on this longitudinal flow within the reaction container by means of an arrangement of successive baffles along the contact tubes which leaves passage cross sections free, so as to give a meandrous flow pattern of the heat-exchange medium in longitudinal section through the tube bundle. This proposal is also included in German Patent 28 30 765, DE-A 2 231 557 and DE-A 2 310 517. Trans I Chem. E, Vol. 71, Part B, August 1993, p. 208 to 214, discloses that complex indirect interactions take place between the heat outputs of the individual contact tubes in exothermic catalytic multiple contact tube fixed-bed oxidations, causing the position of the hot spot and the magnitude thereof generally to differ in the individual contact tubes and being virtually impossible to predict.

In view of this prior art, it is an object of the present invention to provide a novel process for the catalytic gas-phase oxidation of acrolein to acrylic acid in a multiple contact tube fixed-bed reactor through whose space surrounding the contact tubes only one heat-exchange medium circuit is passed, at elevated temperature on catalytically active multimetal oxides, which process is able to give a predetermined acrolein conversion ($\geq 95$ mol % for a single pass) and a predetermined acrylic acid formation selectivity ($\geq 90$ mol %) (ie. a predetermined space-time yield of acrylic acid) for a given acrolein-containing reaction-gas mixture at a given catalyst charge and predetermined acrolein flow rate, in a very simple and favorable manner with formation of reduced hot-spot temperatures.

We have found that this object is achieved by a process for the catalytic gas-phase oxidation of acrolein to acrylic acid in a multiple contact tube fixed-bed reactor through whose space surrounding the contact tubes only one heat-exchange medium circuit is passed, at elevated temperature on catalytically active multi-metal oxides with an acrolein conversion for a single pass of $\geq 95$ mol % and an acrylic acid formation selectivity of $\geq 90$ mol %, which comprises firstly passing the heat-exchange medium through the multiple contact tube fixed-bed reactor longitudinally, considered over the reaction container as a whole, to the contact tubes in cocurrent to the reaction-gas mixture and secondly superposing a transverse flow within the reaction container by means of an arrangement of successive baffles along the contact tubes which leaves passage cross sections free, so as to give a meandrous flow of the heat-exchange medium, seen in longitudinal section through the tube bundle, with the proviso that the flow rate of the circulated heat-exchange medium is set so that its temperature rises by from 2° to 10° C., preferably from 3° to 8° C., very particularly preferably from 4° to 6° C., between the point of entry into the reactor and the point of exit out of the reactor.

German Patent 1 601 162, in column 2, advises against such an embodiment since it makes it impossible to achieve sufficiently uniform tube temperatures over the reactor cross section.

According to the invention, the temperature of the heat-exchange medium on entry into the reactor is selected in a manner known per se so that, for a given catalyst charge and a predetermined acrolein flow rate, the reaction temperature profile necessary in order to achieve the required acrolein conversion and the required acrylic acid selectivity becomes established. The reaction temperatures in such a profile are usually from 200° to 350° C. when the multimetal oxide catalysts comprising molybdenum and vanadium in oxidic form which are known for this purpose are used. Correspondingly, preferred entry temperatures of the heat-exchange medium are from 180° to 300° C. Such suitable multimetal oxide catalysts are mentioned, for example, in U.S. Pat. No. 3,775,474, U.S. Pat. No. 3,954,855, U.S. Pat. No. 3,893,951 and U.S. Pat. No. 4,339,355. Furthermore, the multimetal oxide compositions of EP-A 427 508, DE-A 2 909 671, DE-C 3 151 805, DE-B 2 626 887 and DE-A 4 302 991 are particularly suitable.

A multiplicity of suitable multimetal oxide catalysts can be summarized under the formula I

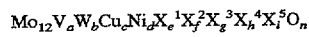 (I)

where $X^1$ is one or more alkali metals,
$X^2$ is one or more alkaline earth metals,
$X^3$ is chromium, manganese, cerium and/or niobium,
$X^4$ is antimony and/or bismuth,
$X^5$ is silicon, aluminum, titanium and/or zirconium,
a is from 1 to 6,
b is from 0.2 to 4,
c is from 0.5 to 6,
d is from 0.2 to 6,
e is from 0 to 2,
f is from 0 to 3,
g is from 0 to 5,
h is from 0 to 40,
i is from 0 to 40, and
n is a number determined by the valency and frequency of the elements other than oxygen.

They are obtainable in a manner known per se (see, for example, DE-A 4 302 991) and are usually shaped in solid form to give spheres, rings or cylinders or alternatively are employed in the form of coated catalysts, ie. preshaped, inert support elements coated with the active material. However, they can of course also be used in powder form as catalysts.

The oxidant used is oxygen. If $N_2$ is chosen as inert diluent gas, the use of air as oxygen source has proven particularly advantageous.

In general, an acrolein:oxygen:steam:inert gas ratio by volume (standard liters) of from 1:(1 to 3):(0 to 20):(3 to 30), preferably from 1:(1 to 3):(0.5 to 10):(7 to 18) is used. The process is normally carried out using acrolein produced by catalytic gas-phase oxidation of propene. In general, the acrolein-containing reaction gases from this propene oxidation are employed without interim purification. The reaction pressure is usually in the range from 1 to 3 bar, and the overall space velocity is preferably from 1000 to 2500 l(s.t.p.)/l/h.

The novel process does not give pure acrylic acid, but a gas mixture from whose secondary components acrylic acid can be separated off in a manner known per se.

With respect to the material, size, number and spacing of the contact tubes and possible heat-exchange media, the comments made above in the assessment of the prior art apply to the novel process. The preferred heat-exchange medium according to the invention is a salt melt consisting of 60% by weight of potassium nitrate ($KNO_3$) and 40% by weight of sodium nitrite ($NaNO_2$).

The transverse flow necessary according to the invention can be generated, for example, by using an arrangement of baffles which leaves a passage cross section free alternately on the opposite sides of the reactor container (cf. for example, DE-B 10 39 040). However, with increasing design capacity of the reactor, in which, due to the large number of contact tubes, the ratio between the diameter and length of the reaction container is also correspondingly large, preference is given to an arrangement of baffles which leaves a passage cross section free alternately in the center and at the outer periphery (additional feature a) (such baffles can be attached, for example, to a rod installed vertically in the center of the reactor), so that the heat-exchange medium is passed successively from the outside inward and from the inside outward. It is advantageous to use tube bundles arranged in an essentially annular manner (where each contact tube advantageously has essentially six equidistant neighbors) with a free central space, where the diameter of the free central space is from about 10 to 30% of the reactor internal diameter (additional feature b). The distance between the outermost contact tubes and the container wall is normally a few centimeters. Furthermore, the contact tubes are preferably not attached to the baffles in a sealing manner. Instead, gaps are advantageously left between the contact tubes and the baffles (gap width generally <1 mm), so that the transverse flow rate of the heat-exchange medium is highly constant within a zone located between two successive baffles (addtional feature c). In combination with different separations of the baffles, it can furthermore advantageously be achieved that the temperature differences (if possible $\leq 3°$ C.) and the pressure drops in a horizontal section within a zone are restricted (additional feature d). Furthermore, it has proven favorable in accordance with the invention if the entry and exit of the heat-exchange medium take place via ring pipelines which are attached to the two ends of the container and have windows distributed over the entire periphery thereof, the window openings being designed in such a way that the same amount of heat-exchange medium passes through each window per time unit (additional feature e), ensuring highly uniform radial supply and removal of the heat-exchange medium (cf. DE-A 16 01 162).

It is also advantageous in accordance with the invention if a part-amount of the heat-exchange medium, preferably from 30 to 70%, particularly preferably from 40 to 60%, of the total amount of heat-exchange medium fed in, is removed from the reactor (for example via a further ring pipeline for removal) at an acrolein conversion of from 20 to 50 mol %, preferably from 30 to 40 mol % (additional feature f). Furthermore, the reaction-gas mixture is preferably fed to the catalyst charge after prewarming to the heat-exchange medium entry temperature (additional feature g). This can be achieved in a simple manner by passing it through a bed of inert material at the appropriate temperature.

In process variants which are particularly advantageous according to the invention, as many as possible of additional features a to g are incorporated simultaneously. Particular preference is given to simultaneous incorporation of all additional features a to g. We assume that, in particular in the last-mentioned procedure, a temperature profile is achieved in the contact tube wall along an individual contact tube where the temperature of the contact tube wall is essentially constant to an acrolein conversion of from 20 to 50 mol % and subsequently increases by from 2° to 10° C. by the end of the tube. We furthermore assume that in this procedure, essentially uniform wall temperatures of the contact tubes also exist over the reactor cross section in the above conversion range.

Quite generally, it is attempted to restrict the number of baffles used. For technical reasons, this number is expediently from 3 to 9.

A reactor type which is suitable for carrying out the particularly advantageous novel process variant is shown by FIG. 1 of DE-B 22 01 528.

It is of course possible to combine the novel procedure for reducing the hot-spot temperature for a predetermined space-time yield with the process proposals mentioned in the description of the prior art.

The novel process has proven particularly favorable if the inert diluent gas in the charging-gas mixture essentially comprises, preferably consists of, combustible gases, as described in the patent application filed in Germany under the file reference 19508531.0. This is particularly true if the charging-gas mixture simultaneously has an increased content by volume of $O_2$ and propylene ("rich procedure"). Inert diluent gases which are preferred in this connection are methane, ethane, propane, butane, pentane and mixtures thereof (cf. in this respect the patent applications filed in Germany under the file references 19508532.9 and 19508558.2).

In this specification, conversion U and selectivity S are defined as follows:

$$U(\text{mol \%}) = \frac{\text{Number of moles of acrolein reacted}}{\text{Number of moles of acrolein employed}} \cdot 100$$

$$S(\text{mol \%}) = \frac{\text{Number of moles of acrolein converted into acrylic acid}}{\text{Number of moles of acrolein reacted in total}} \cdot 100$$

for a single pass.

EXAMPLES

A. Process of the catalytic gas-phase oxidation of acrolein to acrylic acid in a multiple contact tube fixed-bed reactor in which the heat-exchange medium is passed essentially directly longitudinally to the contact tubes (comparative examples).

I. Description of the general process conditions
Heat-exchange medium used: salt melt, consisting of 50% by weight of potassium nitrate and 50% by weight of sodium nitrite;
Contact tube material: ferritic steel;
Dimensions of the contact tubes: length 3200 mm;
internal diameter: 25 mm;
external diameter: 30 mm (wall thickness: 2.5 mm);
Number of contact tubes in tube bundle: 15,700;
Reactor:
Cylindrical container having an internal diameter of 5000 mm;
Homogeneous distribution of the contact tubes over the entire cross section with a contact tube spacing of 38 mm.
The contact tubes were installed with their ends in 100 mm thick tubesheets in a sealing manner and each ran with their openings into a bonnet connected to the container at the upper or lower end.

Feed of heat-exchange medium to the tube bundle: Via a ring channel installed around the reactor container (reactor shell). Flow in the radial direction to the tube bundle via windows installed over the periphery of the reactor shell.

Separating plates (distributor plates) which had a thickness of 10 mm and extended over the entire cross section were installed 25 nun below the upper tubesheet and 25 mm above the lower tubesheet. There were gaps allowing passage between the separating plates and the contact tubes.

The salt melt entered the tube bundle between the lower tubesheet and the lower separating plate and distributed itself over the reactor cross section via the gaps and then rose upward parallel to the contact tubes. On reaching the upper separating plate, the salt melt flowed through the gaps between the separating plate and the contact tubes and then flowed into the space between the upper separating plate and the upper tubesheet radially to the outer circle of tubes and collected, via window passages, in an upper ring channel around the reactor shell and, after cooling to the original entry temperature, was pumped back into the lower ring channel.

The choice of gap widths was made in accordance with German Patent 16 01 162 and DE-B 16 75 501 so that the same hydraulic resistance arose for all stream threads from the lower to the upper ring channel.

Contact tube charge:

Coated catalyst as described in Example B1, of DE-A 43 02 991.

Structure of the charge: (from bottom to top)

400 m bed of naked catalyst supports (steatite beads having a diameter of 5 mm), 800 nm coated catalyst containing 17% by weight of active material, 2000 mm coated catalyst containing 20% by weight of active material.

Flow rate of the reaction-gas mixture:

44750 $m^3$(s.t.p.)/h.

Composition of the reaction-gas mixture:

4.2% by vol. of acrolein, 0.3% by vol. of acrylic acid, 5.5% by vol. of oxygen, 2.4% by vol. of $CO_x$, 6.9% by vol. of $H_2O$, 80.7% by vol. of $N_2$.

Predetermined conversion data:

U=99.5 mol %,

S=95.5 mol %.

Space-time yield:

180 kg of acrylic acid/$m^3$h.

II. Results

The above data were achieved under the following conditions:

| Conditions | Entry temperature of the salt melt | Exit temperature of the salt melt | Hot-spot temperature | Flow of salt pump capacity ($m^3$/h) | melt relative to the reaction gas mixture |
| --- | --- | --- | --- | --- | --- |
| a) | 257° C., Δ = 2° C. | 259° C. | 317° C. | 3800 | Counter-current |
| b) | 263° C., Δ = 1° C. | 264° C. | 307° C. | 7600 | Co-current |
| c) | 259° C., Δ = 2° C. | 261° C. | 311° C. | 3800 | Co-current |
| d) | 248° C., Δ = 5° C. | 253° C. | 327° C. | 1500 | Co-current |

The hot-spot temperature was determined on 5 contact tubes which were selected radially in the tube bundle to be equidistant, from the outermost to the innermost. The temperature given shows the maximum hot-spot value determined.

Countercurrent flow of salt melt and reaction-gas mixture clearly cause the worst hot-spot temperatures.

For cocurrent flow, the hot-spot conditions improve with increasing pump capacity, ie. reducing temperature difference between entry and exit temperature of the salt melt.

Under conditions d), stable, continuous long-term operation of the reactor is no longer possible.

B) Process for the catalytic gas-phase oxidation of acrolein to acrylic acid in a multiple contact tube fixed-bed reactor in which the heat-exchange medium is passed in a meandrous manner in longitudinal section through the contact tube bundle.

I. Description of the general process conditions

Heat-exchange medium used: as for A I;

Number of contact tubes in the tube bundle: 25,500;

Reactor:

Cylindrical container having a diameter of 6800 mm.

Tube bundle in an annular arrangement with a free central space.

Diameter of the central free space: 1000 mm

Distance of the outermost contact tubes from the container wall: 150 mm.

Homogeneous contact tube distribution in the tube bundle (6 equidistant and adjacent tubes per contact tube), contact tube spacing: 38 mm.

The contact tubes were installed with their ends in 125 mm thick tubesheets in a sealing manner and each ran with its opening into a bonnet connected to the container at the upper or lower end.

Feed of the heat-exchange medium to the tube bundle:

The tube bundle was divided into four longitudinal sections (zones) of equal length (in each case 730 mm) by three baffles (each 10 mm thick) installed successively along the tube bundle between the contact tubesheets.

The lowermost and uppermost baffles had ring geometries, the internal diameter of the ring being 1000 mm and the external diameter of the ring extending to the container wall in a sealing manner. Contact tubes were not attached to the baffles in a sealing manner.

Instead, gaps of <0.5 mm were left, so that the transverse flow rate of the salt melt was highly constant within a zone.

The central baffle was circular and extended to the outermost contact tubes of the tube bundle. The circulation of the salt melt was accomplished by two salt pumps, each of which supplied one longitudinal half of the tube bundle.

The pumps forced the salt melt into a lower ring channel around the reactor shell, and this channel distributed the salt melt over the periphery of the container. Windows in the reactor shell allowed the salt melt in the lowermost longitudinal section to pass into the tube bundle. The salt melt then flowed in the sequence, following the baffles, from the outside inward,
from the inside outward,
from the outside inward,
from the inside outward, in an essentially meandrous manner, considered over the container, from bottom to top. Through windows in the uppermost longitudinal section around the container periphery, the salt melt collected in an upper ring channel installed around the reactor shell and, after cooling to the original entry temperature, was pumped back into the lower ring channel.

Contact tube charge, structure of the charge, composition of the reaction mixture and predetermined conversion data: as for A I.

Flow rate of the reaction-gas mixture: 72680 $m^3$(s.t.p.)/h.

II. Results

The predetermined reaction data (conversion, selectivity, space-time yield) were achieved under the following conditions:

| Conditions | Entry temperature of the salt melt | Exit temperature of the salt melt | Hot-spot temperature | pump capacity ($m^3$/h) | Flow of salt melt relative to the reaction gas mixture |
|---|---|---|---|---|---|
| a) | 267° C., $\Delta = 2°$ C. | 269° C. | 308° C. | 6200 | Counter-current |
| b) | 266° C., $\Delta = 2°$ C. | 268° C. | 303° C. | 6200 | Co-current |
| c) | 265° C., $\Delta = 3°$ C. | 268° C. | 301° C. | 4100 | Co-current |
| d) | 263° C., $\Delta = 5°$ C. | 268° C. | 300° C. | 2300 | Co-current |
| e) | 262° C., $\Delta = 8°$ C. | 270° C. | 298° C. | 1500 | Co-current |
| f) | 260° C., $\Delta = 11°$ C. | 271° C. | 303° C. | 100 | Co-current |
| g) | 258° C., $\Delta = 15°$ C. | 273° C. | 306° C. | 800 | Co-current |

The hot-spot temperature was determined on 5 contact tubes selected radially in the tube bundle equidistantly from the outermost to the innermost. The temperatures given show the maximum hot-spot value determined.

Countercurrent flow, considered over the reactor, of salt melt and reaction-gas mixture clearly shows the worst hot-spot temperatures.

Surprisingly, however, the hot-spot behavior passes through a minimum here, in contrast to A), with decreasing pump capacity (increasing difference between entry and exit temperatures of the heat-exchange medium). With decreasing pump capacity, the inhomogeneities in the temperature profile of the reactor (horizontal section) increase, however, which is why, for stability reasons, a $\alpha$ of from 3° to 8° C., preferably from 4° to 6° C., between the entry and exit temperatures of the heat-exchange medium is preferred.

This surprising finding is clearly attributable to the fact that the improved heat exchange caused by the transverse flow component and the increased cooling effect due to the reduced entry temperature of the heat-exchange medium for acrolein conversions of less than 50 mol % improve the hot-spot behavior and the decrease in the space-time yield of acrylic acid which is associated therewith in this section can, surprisingly, be compensated again by the temperature increase, caused by the heat of reaction, at acrolein conversions above 50 mol %. One cause of this result may well be that the heat-transfer coefficient on the heat-transfer side of the reaction tubes surprisingly clearly does not decrease to the same extent as the decrease in pump capacity.

A further improvement is therefore possible by removing a part-amount, preferably from 30 to 70 mol % of the feed amount, of the heat-exchange medium at an acrolein conversion of from 20 to 50 mol %. This causes even better relative cooling and homogenization of the temperature over a reactor cross section at relatively low conversions and at the same time a greater relative temperature increase at high conversions.

At a salt melt feed temperature of 264° C. and a reduction in the circulated amount of salt melt from 5,400 $m^3$/h to 2,300 $m^3$/h (part-amount removed=57%) at the first baffle (flow-control valve) (acrolein conversion=about 35 mol %), a hot-spot temperature of 297° C. with an exit temperature of 269° C. results under otherwise identical conditions, as stated under B. At the same time, a procedure of this type improves the homogeneity of the temperature profile of the reactor (horizontal section) and the homogeneity of the positions of the hot spots in the individual contact tubes. Decreasing the pump capacity results in considerable costs reduction.

Furthermore, the result in accordance with the invention allows the option either of achieving a longer service life of the catalyst charge at a given space-time yield due to the better hot-spot situation or achieving an increased space-time yield for a given service life by increasing the flow rate.

We claim:

1. A process for the catalytic gas-phase oxidation of acrolein to acrylic acid in a multiple contact tube fixed-bed reactor through whose space surrounding the contact tubes only one heat-exchange medium circuit is passed, at elevated temperature on catalytically active multimetal oxides with an acrolein conversion for a single pass of $\geq 95$ mol % and an acrylic acid formation selectivity of $\geq 90$ mol %, which comprises firstly passing the heat-exchange medium through the multiple contact tube fixed-bed reactor longitudinally, considered over the reaction container as a whole, to the contact tubes in cocurrent to the reaction-gas mixture and secondly super-posing a transverse flow within the reaction container by means of an arrangement of successive baffles along the contact tubes which leaves passage cross sections free, so as to give a meandrous flow of the heat-exchange medium, seen in longitudinal section through the contact tube bundle, and setting the flow rate of the circulated heat-exchange medium so that its temperature rises by from 2° to 10° C. between the point of entry into the reactor and the point of exit out of the reactor.

2. A process as claimed in claim 1, wherein the temperature of the heat-exchange medium rises by from 3° to 8° C. between the point of entry into the reactor and the point of exit out of the reactor.

3. A process as claimed in claim 1, wherein the temperature of the heat-exchange medium rises by from 4° to 6° C. between the point of entry into the reactor and the point of exit out of the reactor.

4. A process as claimed in claim 1, wherein an arrangement of baffles is used which leaves a passage cross section free alternately in the center and at its outer periphery.

5. A process as claimed in claim 1, wherein tube bundles having a free central space which are arranged in an essentially annular manner are used.

6. A process as claimed in claim 5, wherein the diameter of the free central space is from about 10 to 30% of the reactor internal diameter.

7. A process as claimed in claim 1, wherein the contact tubes are not attached to the baffles in a sealing manner, but instead gaps are left between the contact tubes and the baffles.

8. A process as claimed in claim 7, wherein the gap widths are set so that the transverse flow rate of the heat-exchange medium within a zone located between two successive baffles is very constant.

9. A process as claimed in claim 1, wherein a non-equidistant arrangement of the baffles restricts the temperature differences and the pressure drops in a horizontal section within a zone.

10. A process as claimed in claim 1, wherein the entry and exit of the heat-exchange medium take place via ring pipelines which are attached to the two ends of the reactor container and have windows distributed over the entire periphery thereof, the window openings being designed in such a way that the same amount of heat-exchange medium passes through each window per time unit.

11. A process as claimed in claim 1, wherein a part-amount of heat-exchange medium is removed from the reactor at an acrolein conversion of from 20 to 50 mol %.

12. A process as claimed in claim 11, wherein the removal takes place at an acrolein conversion of from 30 to 40 mol %.

13. A process as claimed in claim 11 or 12, wherein the part-amount of heat-exchange medium removed is from 30% to 70% of the total amount of heat-exchange medium fed in.

14. A process as claimed in claim 1, wherein the reaction-gas mixture is fed to the catalyst charge after being prewarmed to the entry temperature of the heat-exchange medium.

15. A process as claimed in claim 1, wherein an arrangement of baffles is used which leaves a passage cross section free alternately in the center and at its outer periphery, and wherein tube bundles having a free central space which are arranged in an essentially annular manner are used and the diameter of the free central space is from about 10 to 30% of the reactor internal diameter, and wherein the contact tubes are not attached to the baffles in a sealing manner, but instead gaps are left between the contact tubes and the baffles and the gap widths are set so that the transverse flow rate of the heat-exchange medium within a zone located between two successive baffles is very constant, and wherein a non-equidistant arrangement of the baffles restricts the temperature differences and the pressure drops in a horizontal section within a zone, and wherein the entry and exit of the heat-exchange medium take place via ring pipelines which are attached to the two ends of the reactor container and have windows distributed over the entire periphery thereof, the window openings being designed in such a way that the same amount of heat-exchange medium passes through each window per time unit, and wherein a part-amount of heat-exchange medium is removed from the reactor at an acrolein conversion of from 20 to 50 mol % and the part-amount of heat-exchange medium removed is from 30% to 70% of the total amount of heat-exchange medium fed in, and wherein the reaction-gas mixture is fed to the catalyst charge after being prewarmed to the entry temperature of the heat-exchange medium.

16. A process as claimed in claim 1, wherein the catalyst charge comprises a multimetal oxide catalyst comprising molybdenum and vanadium in oxidic form.

17. A process as claimed in claim 1, wherein the heat-exchange medium is a salt melt consisting of 60% by weight of potassium nitrate ($KNO_3$) and 40% by weight of sodium nitrite ($NaNO_2$).

* * * * *

UNITED STATES PATENT AND TRADEMARK OFFICE
CERTIFICATE OF CORRECTION

PATENT NO. : 5,739,391
DATED : April 14, 1998
INVENTOR(S) : Wilhelm RUPPEL ET AL It is certified that error appears in the above-identified patent and that said Letters Patent is hereby corrected as shown below:

Column 6, line 22 "has proven" should read --is--.

line 46 insert --The data present in the illustrative examples that follow are derived from arithmetic simulation, not actual experiment.-- line 52 delete "used".

line 66 "were" should read --are--.

Column 7, line 1 "ran" should read --runs--.

line 4 delete "installed".

line 6 delete "installed".

line 7 "had" should read --have--.

lines 8 and 9 "extended over the entire cross section were" should read --extend over the entire cross section are--.

line 11 "were" should read --are--.

line 13 "entered" should read --enters--.

line 14 "distributed" should read --distributes--.

line 15 "rose" should read --rises--.

line 17 "flowed" should read --flows--.

UNITED STATES PATENT AND TRADEMARK OFFICE
CERTIFICATE OF CORRECTION

PATENT NO. : 5,739,391
DATED : April 14, 1998
INVENTOR(S) : Wilhelm RUPPEL ET AL It is certified that error appears in the above-identified patent and that said Letters Patent is hereby corrected as shown below:

Column 7, line 19 "flowed" should read --flows--.

line 21 "collected" should read --collects--.

line 23 "was" should read --is--.

line 25 "was" should read --is--.

line 27 "arose" should read --arises--.

line 57 "were" should read --is--.

Column 8, line 14 "was" should read --is--.

line 15 "were" should read --are--.

lines 18 and 19 delete "determined".

line 27 "is passed" should read --passes--.

line 31 delete "used".

line 43 "were" should read --are--.

line 45 "ran" should read --runs--.

line 49 "was" should read --is--.

line 51 delete "installed".

line 58 "were" should read --are--.

line 60 "were" should read --are--.

UNITED STATES PATENT AND TRADEMARK OFFICE
CERTIFICATE OF CORRECTION

PATENT NO. : 5,739,391  
DATED : April 14, 1998  
INVENTOR(S) : Wilhelm RUPPEL ET AL Page 3 of 4

It is certified that error appears in the above-identified patent and that said Letters Patent is hereby corrected as shown below:

Column 8, line 61 "was" should read --is--.

line 63 "was circular and extended" should read --is circular and extends--.

line 65 "was" should read --is--.

line 66 "supplied" should read --supplies--.

Column 9, line 1 "forced" should read --force--.

line 3 "distributed" should read --distributes--.

line 4 "allowed" should read --allows--.

line 7 "flowed" should read --flows--.

UNITED STATES PATENT AND TRADEMARK OFFICE
CERTIFICATE OF CORRECTION

PATENT NO. : 5,739,391
DATED : April 14, 1998
INVENTOR(S) : Wilhelm RUPPEL ET AL It is certified that error appears in the above-identified patent and that said Letters Patent is hereby corrected as shown below:

Column 9, line 15 "collected" should read --collects--.

line 17 "after cooling" should read --is cooled--.

line 18 "was" should read --is--.

line 27 "were" should read --are--.

line 50 "was" should read --is--.

line 53 delete "determined".

Signed and Sealed this

Twenty-ninth Day of December, 1998

Attest:

BRUCE LEHMAN

Attesting Officer

Commissioner of Patents and Trademarks